United States Patent [19]

Yamada

[11] 4,032,685

[45] June 28, 1977

[54] ARTIFICIAL HAIR

[76] Inventor: Shiro Yamada, No. 31-8, Koboyama, Kobo-cho, Chiryu, Aichi, Japan

[22] Filed: June 3, 1976

[21] Appl. No.: 692,305

[30] Foreign Application Priority Data

Aug. 1, 1975 Japan .............. 50-105798[U]

[52] U.S. Cl. .............. 428/399; 264/148; 264/177 F; 264/210 F; 428/400; 428/401
[51] Int. Cl.² .............. A41G 5/00; D01D 5/12
[58] Field of Search .......... 428/397, 399, 400, 401; 264/148, 177 F, 210 F

[56] References Cited

UNITED STATES PATENTS

| 2,207,157 | 7/1940 | Neville et al. | 428/399 |
| 2,746,839 | 5/1956 | Terry et al. | 428/397 |
| 3,256,545 | 6/1966 | Lewis et al. | 428/399 |
| 3,684,474 | 8/1972 | Chisholm | 65/105 |
| 3,691,749 | 9/1972 | McKay | 428/397 |

Primary Examiner—J.C. Cannon
Attorney, Agent, or Firm—Browdy and Neimark

[57] ABSTRACT

An artificial hair consisting essentially of a monofilament having a corollaceous cross-section, and a root formed at one end of the monofilament having a corollaceous cross-section larger than that of the monofilament proper.

9 Claims, 6 Drawing Figures

ARTIFICIAL HAIR

BACKGROUND OF THE INVENTION

The present invention relates to artificial hairs which may be implanted on the human skin or the like, and more particularly to a method of preparing said artificial hairs.

The present inventor has already created techniques for implanting artificial hairs on the human skin, noting copending application Ser. No. 581,961 now U.S. Pat. No. 4,004,592. The present invention relates to artificial hairs optimum for such techniques. For better understanding of the aim of the invention, the artificial hair implanting technique will briefly be described below.

Referring to FIG. 1, a needle 4 having its point shaped like a fork 5 is used to hold an artificial hair 1 at the boundary between the hair proper 2 and its root 3. The root is then thrust into the dermal tissue 7 or the hypodermal tissue 8 by forcing the needle 4 through the epidermis 6. In the tissue, the root 3 turns back as the needle point advances, thus serving as a hook with the root being totally implanted in the skin and aligned largely perpendicular to the plane of the skin. The needle point, when thrusted, will, of course, cut the tissue. The so cut area, virtually a tiny spot of cut, is healed in a few days. In the process of restoration, the tissue about the root becomes reinforced to retain the root firmly in position. The needle point is not necessarily of the fork design but other needle points may be employed.

SUMMARY OF THE INVENTION

It is an object of the invention to provide an artificial hair suited for implantation on the human skin or the like.

Another object of the invention is to provide a suitable method of preparing the artificial hair suited for implantation on the human skin or the like.

With this and other objects in view, the invention provides an artificial hair constituted virtually of a monofilament having a corollaceous cross-section, and a root formed at one end of the monofilament having a corollaceous cross-section larger than that of the monofilament proper.

The method of the present invention pertaining to the preparation of such artificial hair comprising melt-spinning thermoplastic resins, such as polyamides, polyesters, polyethylenes or polyvinyl chlorides by a spinning nozzle having a star-shaped cross-section thereby obtaining a monofilament of corollaceous cross-section, drawing said monofilament strongly such as at the ratio of about 1:3 – 1:5 in length, cutting said drawn monofilament in a suitable length and heating instantaneously one end of said cut piece of monofilament at a softening temperature, for example within the range from 150° C to 200° C, by a heater thereby obtaining the root having a corollaceous cross-section with a diameter about the same as that of the initial monofilament.

Further objects, features and advantages of the invention will become more apparent from the following description when read in conjunction with the accompanying drawings, wherein:

DESCRIPTION OF THE PREFERRED EMBODIMENT

Figure 3:
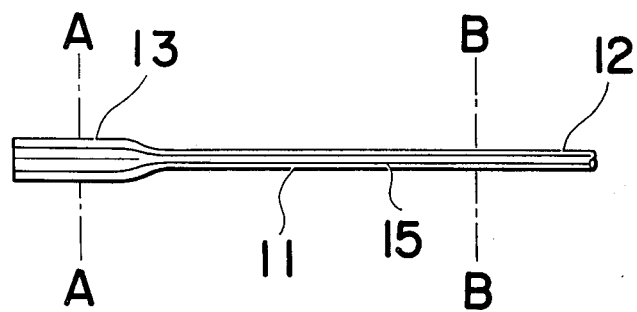
FIG. 3 is a side view showing an artificial hair of the invention.
Figure 4:
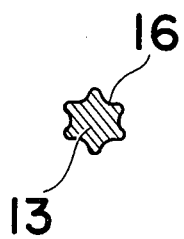
FIG. 4 is a cross-sectional view through A—A of FIG. 3.
Figure 5:
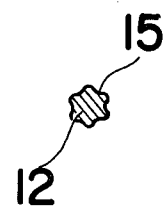
FIG. 5 is a cross-sectional view through B—B of FIG. 3.
Figure 6:
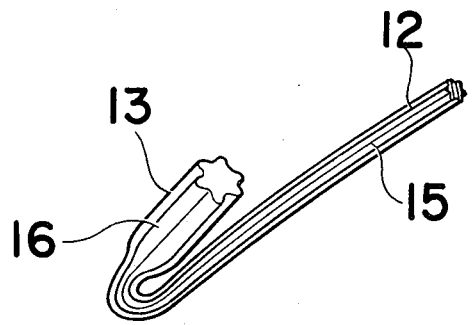
FIG. 6 is a perspective schematic view showing an artificial hair of the invention with its root turned back.

The artificial hair of the invention is constituted essentially of a monofilament consisting of a hair proper 12 having a corollaceous cross-section, and a root 13 formed at one end of the hair proper 12, having a corollaceous cross-section larger than that of the hair proper 12, as shown in FIG. 3. In this particular embodiment, the cross-sections of the hair proper 12 and the root 13 are in the shape of 6 corollas as shown in FIGS. 4 and 5. The number of corollas is not limited to six but may arbitrarily be determined; according to the invention, it is preferably 5 to 8 from the viewpoint of monofilament productivity and for the purpose of the invention in relation to the corollaceous cross-section of the artificial hair. This implanting artificial hair is advantageous over one having a circular cross-section by the following reasons.

Figure 1:
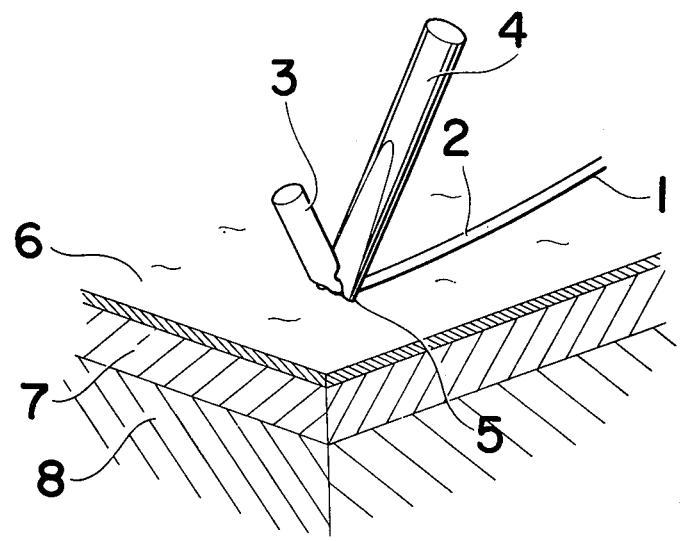
FIG. 1 is a schematic diagram for illustrating an artificial hair implanting method.
Figure 2:
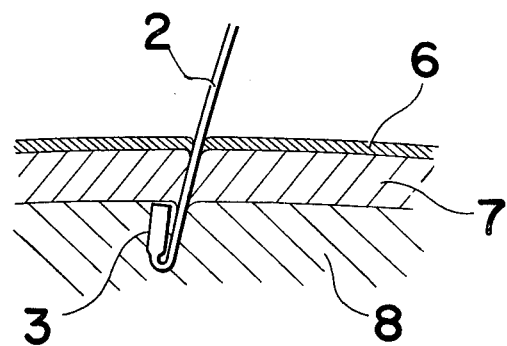
FIG. 2 is a cross-sectional view showing an implanted artificial hair.

When an artificial hair is implanted on the human skin in the manner shown in FIGS. 1 and 2, the hypodermic tissue is excited to cause an exudation, e.g., lymph, to be oozed, which serves to force out the root of the hair. Whereas, as shown in FIGS. 3 and 4, grooves 15 are formed along the surface of the hair proper 12 into a corollaceous cross-section, and the exudation is readily led out of the hypodermic tissue by way of the grooves 15 and evaporated on the outer skin, with the result that the root 13 is prevented from being forced out due to the exudation, and the root 13 can establish closer contact with the surrounding hypodermic tissue and serve to urge the growth of connective tissue. The connective tissue comes in close contact with the surfaces of the grooves 15 on the hair proper 12 in the portion buried in the hypodermic tissue and of the surfaces of the grooves 16 on the root 13, thus permitting the hair to be securely retained in position.

The prior art artificial hair of circular cross-section is impractical in that the neck of the root is not sufficiently bent, or the root does not function as a stopper, causing the implanted hair to become loose or to be cut at the neck thereof.

Whereas, according to the invention, the internal stress produced in the neck thereof when the root is turned back is adsorbed by the grooves 15. This enables the root to be sufficiently turned back without weakening the neck. Furthermore, the lugs of the corrollas as in FIGS. 4 and 5 serves as ribs which increase the mechanical strength of the artificial hair, thus preventing the hair from falling or from being cut at the neck.

The grooves 15 on the hair reflect light diffusely and hence the artificial hair looks very much like natural hair. Still further, the grooves 15 permit the artificial hair to be as smooth as natural hair when touched. Furthermore, the grooves 15 serve as capillaries and increase the area of the surface of the hair, thus urging sweat evaporation. In addition, the grooves 15 can withhold an excess amount of hair-fixer to prevent the artificial hairs from becoming sticky to each other and to the skin, as opposed to the fact that artificial hairs without grooves 15 tend to become sticky when a hair-fixer is applied. In other words, the artificial hairs with grooves 15, when implanted, can be shaped to the desired style as in the case of natural hair.

To be an ideal substitute for natural hair, the artificial hair of the invention should have substantially the same dimensions as natural hair. Typically the following dimensions are observed:

Diameter of the hair proper: 0.06 to 0.1mm
Diameter of the root: 0.13 to 0.2mm
Length of the root: 1.0 to 1.5mm This artificial hair is fabricated in the following manner. A thermoplastic resin such as polyamide, polyester, polyethylene and polyvinyl chloride is used as the material of the hair. A monofilament is spun out of the hight polymerized polyvinyl chloride of which degree of polymerization 800 – 1200 by usual melt-spinning process in which a spinning nozzle having a star-shaped cross-section is used to obtain the monofilament of corollaceous cross-section.

After spinning process, this monofilament is cooled by water and then is drawn in drawing process to a length at the ratio of about 1:4 and then cut to the prescribed length. One end of the cut piece of monofilament is instantaneously heated to a temperature of about 180° C by an electric heater whereby a root is formed. Because the monofilament drawn under a certain forced strength returns to its initial state when it is heated, the root assumes a corollaceous cross-section with a diameter about the same as that of the initial monofilament.

While one preferred embodiment of the invention has been described above, it is to be understood that the invention is not limited to the disclosed example but numerous variations may occur to those skilled in the art without departing from the true spirit of the invention.

What is claimed is:

1. An artificial hair having a hair portion of diameter substantially the same as that of natural hair constituted essentially of a monofilament of thermoplastic resin having a corollaceous cross-section, and an elongated root portion integrally formed at one end of the monofilament and having a corollaceous cross-section larger than that of said hair portion, said elongated root portion being of length to render said root portion totally implantable in the skin while aligned largely perpendicular to the plane of the skin.

2. An artificial hair in accordance with claim 1, wherein said thermoplastic is a polyamide, a polyester, or polyethylene.

3. An artificial hair in accordance with claim 1, wherein the diameter of said hair portion is about 0.06 to 0.1 mm, the diameter of said root portion is about 0.13 to 0.2 mm, and the length of said root portion is about 1.0 to 1.5 mm.

4. An artificial hair in accordance with claim 1, having 5–8 corollas.

5. An artificial hair in accordance with claim 4, wherein the diameter of said hair portion is about 0.06 to 0.1 mm.

6. An artificial hair in accordance with claim 4, wherein the diameter of said root portion is about 0.13 to 0.2 mm.

7. An artificial hair in accordance with claim 6, wherein the length of said root portion is about 1.0 to 1.5 mm.

8. A method of preparing artificial hair constituted essentially of a monofilament of thermoplastic resin having a corollaceous cross-section and a root formed at one end of the monofilament having a corollaceous cross-section larger than that of the monofilament proper which comprising:

melt-spinning a thermoplastic resin by a spinning nozzle having a star-shaped cross-section thereby obtaining a monofilament of corollaceous cross-section, drawing strongly said monofilament in a drawing process, cutting said drawn monofilament to a suitable length and heating instantaneously one end of said cut piece of monofilament at a softening temperature of said plastics thereby obtaining the root having a corollaceous cross-section with approximately the same diameter as that of the undrawn monofilament.

9. A method of preparing the artificial hair in accordance with claim 8 wherein the draw ratio in said drawing process is from 1:3 – 1:5 in length.

* * * * *